(12) United States Patent
Hart et al.

(10) Patent No.: US 12,226,158 B2
(45) Date of Patent: Feb. 18, 2025

(54) SYSTEMS FOR OFF-AXIS IMAGING OF A SURFACE OF A SAMPLE AND RELATED METHODS AND COMPUTER PROGRAM PRODUCTS

(71) Applicant: Leica Microsystems NC, Inc., Durham, NC (US)

(72) Inventors: Robert H. Hart, Cary, NC (US); Dorothy M. Branco, Durham, NC (US); Eric L. Buckland, Hickory, NC (US); Micaela R. Mendlow, Jersey City, NJ (US)

(73) Assignee: LEICA MICROSYSTEMS NC, INC., Durham, NC (US)

( * ) Notice: Subject to any disclaimer, the term of this patent is extended or adjusted under 35 U.S.C. 154(b) by 745 days.

(21) Appl. No.: 17/424,056

(22) PCT Filed: Mar. 19, 2020

(86) PCT No.: PCT/US2020/023544
§ 371 (c)(1),
(2) Date: Jul. 19, 2021

(87) PCT Pub. No.: WO2020/191148
PCT Pub. Date: Sep. 24, 2020

(65) Prior Publication Data
US 2022/0125301 A1    Apr. 28, 2022

Related U.S. Application Data

(60) Provisional application No. 62/821,556, filed on Mar. 21, 2019.

(51) Int. Cl.
*A61B 3/10*     (2006.01)
*A61B 3/00*     (2006.01)
*G06T 7/33*     (2017.01)

(52) U.S. Cl.
CPC ............ *A61B 3/102* (2013.01); *A61B 3/0025* (2013.01); *G06T 7/344* (2017.01); *G06T 2207/10101* (2013.01); *G06T 2207/30041* (2013.01)

(58) Field of Classification Search
CPC ......... A61B 3/102; A61B 3/0025; A61B 3/13; A61B 3/107; A61B 3/1216; A61B 3/1225;
(Continued)

(56) References Cited

U.S. PATENT DOCUMENTS 4,050,192 A * 9/1977 Volk ...................... B24B 13/065
                                                  451/240
5,042,951 A * 8/1991 Gold ................... G03F 7/70633
                                                  356/369
(Continued)

FOREIGN PATENT DOCUMENTS

CN    104050703 A    9/2014
CN    104334072 A    2/2015
(Continued)

OTHER PUBLICATIONS

Office Action, Japanese Patent Application No. 2021-0544266, Jul. 13, 2022, 13 pages.
(Continued)

*Primary Examiner* — Travis S Fissel
(74) *Attorney, Agent, or Firm* — LEYDIG, VOIT & MAYER, LTD.

(57) ABSTRACT

Systems for determining an apex of curvature In an image, obtained from, a sample are provided. The systems include —an imaging system configured to obtain a plurality of scans of a sample using a radial pattern; and a processor associated with the imaging system. The processor is configured to segment and curve fit each of the plurality of scans (Continued)

to a surface of the sample; determine an apex. for each curve associated with each of the plurality of scans; determine a true apex, among all determined apexes using a derivative of least value; calculate an XY offset based on the determined true apex; map the true apex to an origin where X and Y are equal to zero; and adjust the coordinates associated with remaining apexes not determined to be the true apex based on the calculated offset.

20 Claims, 9 Drawing Sheets

(58) Field of Classification Search
CPC ....... A61B 3/103; A61B 3/1035; A61B 3/117; A61B 3/1173; A61B 3/18; G06T 7/344; G06T 2207/10101; G06T 2207/30041; G06T 2207/30004
USPC .......................................... 351/205, 210–212
See application file for complete search history.

(56) References Cited

U.S. PATENT DOCUMENTS

| | | |
|---|---|---|
| 2005/0157311 A1 | 7/2005 | Kuchel |
| 2009/0268020 A1 | 10/2009 | Buckland et al. |
| 2011/0149245 A1 | 6/2011 | Barth et al. |
| 2013/0188140 A1 | 7/2013 | Bagherinia et al. |
| 2013/0235343 A1* | 9/2013 | Hee .................. A61B 3/102 351/206 |
| 2013/0265545 A1 | 10/2013 | Buckland et al. |
| 2014/0267252 A1 | 9/2014 | Hutchinson et al. |
| 2015/0092160 A1* | 4/2015 | Chen .................. A61B 3/102 351/206 |
| 2018/0014725 A1* | 1/2018 | Bagherinia .......... G06T 7/215 |
| 2018/0192866 A1 | 7/2018 | Abou Shousha et al. |

FOREIGN PATENT DOCUMENTS

| | | |
|---|---|---|
| CN | 109143344 A | 1/2019 |
| JP | 2013-176497 A | 9/2013 |
| JP | 2015-509433 A | 3/2015 |
| JP | 2015043855 A | 3/2015 |
| JP | 2015-066083 A | 4/2015 |
| WO | 2010017954 A2 | 2/2010 |
| WO | WO 2017/190087 A1 | 11/2017 |

OTHER PUBLICATIONS

McNabb et al., Distributed scanning volumetric SDOCT for motion corrected corneal biometry, Biomedical Optics Express, vol. 3, No. 9, Aug. 10, 2012, pp. 2050-2154.

Zhao et al., "3D refraction correction and extraction of clinical parameters from spectral domain optical coherence tomography of the cornea," Optic Express, vol. 18, Jan. 1, 2010, pp. 8923-8936.

International Search Report and Written Opinion, PCT/US2020/023544, Jun. 24, 2020, 10 pages.

Xu Jixiang et al., "Several related concepts about depth migration," Petroleum Geophysical Exploration, vol. 39, issue 3, Jun. 15, 2004, Tongfang CNKI (Beijing) Technology Co., Ltd, China, pp. 259-264.

Duan PF, Cheng JB, Chen SP, et al. Local angle-domain ray tracing and prestack depth migration in TI medium. Chinese J. Geophysics (in Chinese), 2013 56(1): 269-279, doi:10.6038/cjg20130128, Jan. 2013, China.

* cited by examiner

SYSTEMS FOR OFF-AXIS IMAGING OF A SURFACE OF A SAMPLE AND RELATED METHODS AND COMPUTER PROGRAM PRODUCTS

CROSS-REFERENCE TO RELATED APPLICATIONS

The present application is a U.S.C. § 371 national phase application of PCT International Application No. PCT/US2020/023544, filed Mar. 19, 2020, which claims priority to U.S. Provisional Patent Application No. 62/821,556, filed Mar. 21, 2019. The disclosures of each are hereby incorporated herein by reference in their entireties.

STATEMENT OF GOVERNMENT SUPPORT

This inventive concept was funded in-part with government support under the GAANN Fellowship by the DOE. The United States Government has certain rights in this inventive concept.

FIELD

The present inventive concept relates generally to imaging systems and, more particular, to imaging of a curved surface of a sample and related systems and devices.

BACKGROUND

Surgical microscopes provide a magnified view of the operating field to the surgeon. Ophthalmic surgical microscopes are commonly stereo zoom microscopes with binocular view ports for the surgeon, and frequently have one or two observer view ports at ninety degrees (left and right) to the surgeon. The working distance between the objective lens of the microscope and the surface of a patient eye may range, for example, from about 100 mm to about 200 mm in order to allow the surgeon sufficient working area. However, working distances may vary.

Surgical microscopes are tailored to provide clear optical view to the subject, with uniform illumination and accurate color temperature. Stereo microscopes provide a degree of parallax to provide the surgeon with a sense of space and topography. Occasionally dyes are used to emphasize topography. High definition video is being offered into surgical microscopes to improve visual clarity. Topographic three-dimensional (3D) video technologies adopted from entertainment industry, such as polarization-diversity stereoscopy, are now being added to increase the sense of depth.

Such surgical stereo microscopes may be constrained to surface visualization. Optical coherence tomography (OCT) is now a well-established technology for imaging beneath an optically translucent surface. High resolution OCT offers a capability to observe sub-surface structures, complementary to the surface views of stereo, high definition and 3D surgical microscopes. Optical coherence tomography is a standard of care in retinal diagnostics and is finding some use in cornea imaging and metrology OCT is only beginning to find use in intra-surgical imaging. Bioptigen offers a handheld ophthalmic OCT system that has been cleared by the Food and Drug Administration ("FDA") for imaging patients under anesthesia. This device is finding application in handheld and mounted configurations for structural imaging during ophthalmic surgeries, including retinal surgery and cornea transplant surgery and an adjunct to surgeon's microscope visualization.

SUMMARY

Some embodiments of the present inventive concept provide systems for determining an apex of curvature in an image obtained from a sample. The systems include an imaging system configured to obtain a plurality of scans of a sample using a radial pattern; and a processor associated with the imaging system. The processor is configured to segment and curve fit each of the plurality of scans to a surface of the sample; determine an apex for each curve associated with each of the plurality of scans; determine a true apex among all determined apexes using a derivative of least value; calculate an XY offset based on the determined true apex; map the true apex to an origin where X and Y are equal to zero; and adjust the coordinates associated with remaining apexes not determined to be the true apex based on the calculated offset.

In further embodiments, after calculating the offset, the processor may be further configured to assess a degree of noise present in the plurality of scans, noise being one of random noise and non-random noise; and if the noise present is determined to not be tolerable, the imaging system is configured to auto-shift a scan origin based on the calculated offset and rescan the sample or discard the plurality of scans and rescan the sample.

In still further embodiments, the processor may be further configured to calculate an arctangent of a slope of a curve of a scanning beam of the imaging system to provide an angle of incidence; and apply the angle of incidence to a refractive calculation and thickness measurement.

In some embodiments, the plurality of scans may be a plurality of b-scans of the sample and the imaging system may be configured to obtain the plurality of b-scans using a radial scan with a rotation axis.

In further embodiments, the processor may be further configured to plot each of the determined apexes for each curve associated with each of the plurality of scans to create an ellipse when plotted on an XY coordinate plane and wherein one of plotted apexes comprises the true apex.

In still further embodiments, the sample may be a cornea of an eye of a subject.

In some embodiments, the imaging system may be an optical coherence tomography imaging system.

Related methods and computer program products are provided.

DETAILED DESCRIPTION

Figure 1:
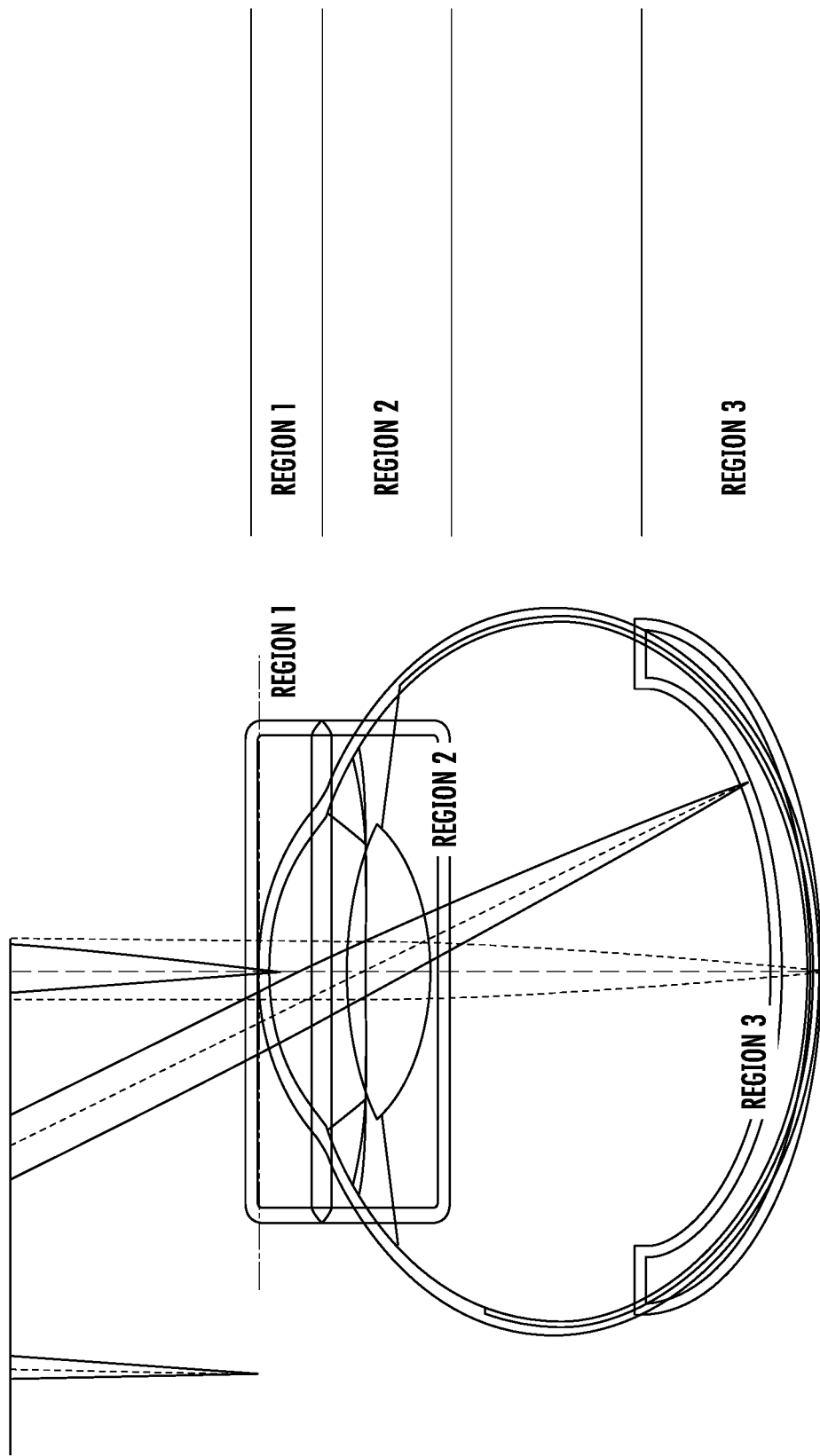
FIG. 1 is a diagram illustrating the various regions of the eye.

The present inventive concept will be described more fully hereinafter with reference to the accompanying figures, in which embodiments of the inventive concept are shown. This inventive concept may, however, be embodied in many alternate forms and should not be construed as limited to the embodiments set forth herein.

Accordingly, while the inventive concept is susceptible to various modifications and alternative forms, specific embodiments thereof are shown by way of example in the drawings and will herein be described in detail. It should be understood, however, that there is no intent to limit the inventive concept to the particular forms disclosed, but on the contrary, the inventive concept is to cover all modifications, equivalents, and alternatives falling within the spirit and scope of the inventive concept as defined by the claims. Like numbers refer to like elements throughout the description of the figures.

The terminology used herein is for the purpose of describing particular embodiments only and is not intended to be limiting of the inventive concept. As used herein, the singular forms "a", "an" and "the" are intended to include the plural forms as well, unless the context clearly indicates otherwise. It will be further understood that the terms "comprises", "comprising," "includes" and/or "including" when used in this specification, specify the presence of stated features, integers, steps, operations, elements, and/or components, but do not preclude the presence or addition of one or more other features, integers, steps, operations, elements, components, and/or groups thereof. Moreover, when an element is referred to as being "responsive" or "connected" to another element, it can be directly responsive or connected to the other element, or intervening elements may be present. In contrast, when an element is referred to as being "directly responsive" or "directly connected" to another element, there are no intervening elements present. As used herein the term "and/or" includes any and all combinations of one or more of the associated listed items and may be abbreviated as "/".

Unless otherwise defined, all terms (including technical and scientific terms) used herein have the same meaning as commonly understood by one of ordinary skill in the art to which this inventive concept belongs. It will be further understood that terms used herein should be interpreted as having a meaning that is consistent with their meaning in the context of this specification and the relevant art and will not be interpreted in an idealized or overly formal sense unless expressly so defined herein.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element without departing from the teachings of the disclosure. Although some of the diagrams include arrows on communication paths to show a primary direction of communication, it is to be understood that communication may occur in the opposite direction to the depicted arrows.

Aspects of the present disclosure are described herein with reference to flowchart illustrations and/or block diagrams of methods, apparatuses (systems) and computer program products according to embodiments of the disclosure. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable instruction execution apparatus, create a mechanism for implementing the functions/acts specified in the flowchart and/or block diagram block or blocks. As used herein, "a processor" may refer to one or more processors.

These computer program instructions may also be stored in a computer readable medium that when executed can direct a computer, other programmable data processing apparatus, or other devices to function in a particular manner, such that the instructions when stored in the computer readable medium produce an article of manufacture including instructions which when executed, cause a computer to implement the function/act specified in the flowchart and/or block diagram block or blocks. The computer program instructions may also be loaded onto a computer, other programmable instruction execution apparatus, or other devices to cause a series of operational steps to be performed on the computer, other programmable apparatuses or other devices to produce a computer implemented process such that the instructions which execute on the computer or other programmable apparatus provide processes for implementing the functions/acts specified in the flowchart and/or block diagram block or blocks.

Although many of the examples discussed herein refer to the sample/subject being an eye, specifically, the retina, cornea, anterior segment and lens of the eye, embodiments of the present inventive concept are not limited to this type of sample. Any type of sample that may be used in conjunction with embodiments discussed herein may be used without departing from the scope of the present inventive concept.

Although embodiments of the present inventive concept focus on the use of Optical Coherence Tomography (OCT) to scan the sample, embodiments of the present inventive concept are not limited to the use of OCT. It will be understood that any method and system that uses a radial pattern to scan a sample can be used without departing from the scope of the present inventive concept.

Furthermore, imaging as discussed herein can be performed in any manner known to those having skill in the art. For example, in some embodiments the imaging system may be incorporated into a microscope or surgical microscope, may be used to precisely calibrate a prescription of an artificial lens and the like. Various of these embodiments are discussed in, for example, U.S. Pat. No. 8,77,412 and U.S. Patent Publication Nos. 2015/0168250 and 2015/0359426, the disclosures of which are incorporated herein by reference as if set forth in its entirety.

As used herein, "subject" refers to a person, portion of person or thing being imaged. It will be understood that although embodiments of the present inventive concept are discussed herein with respect to an eye being the subject, embodiments of the present inventive concept are not limited to this configuration. The subject can be any subject, including, for example, veterinary, cadaver study or human subject without departing from the scope of the present inventive concept.

When calculating thicknesses using the refractive properties (i.e. Snell's law) of light and a transparent material, both the refractive index of the material and the incident angle of the light (i.e. the scanning beam) relative to the surface curvature must be known to a high degree of accuracy. In the case of measuring the thickness of the cornea, the surface curvature and the location of the scanning beam relative to the Apex of the curvature is used to correctly determine the true angle of incidence to the tissue surface. The movement of the subject during the imaging process introduces noise into the thickness measurement. For example, when imaging an eye, the eye will pulsate as there is blood flowing in the body of the subject. This pulsation may cause a distortion in the resulting thickness map. Therefore, removal of the resultant inaccuracies of the thickness calculation is performed to ensure the actual or true angle of incidence is used in the refractive calculation. By calculating the offsets for each Apex as discussed in greater detail herein below, the corresponding change in angle of incidence can be determined and applied to the refractive calculation for improved accuracy of the thickness measurements.

Referring first to FIG. 1, a diagram of an eye illustrating various regions thereof will be discussed. As illustrated in FIG. 1, there are various regions of interest in the eye, which may require different imaging characteristics. For example, using OCT imaging characteristics as an example, REGION 1, the corneal region, typically requires relatively high-resolution OCT imaging. A fairly large depth-of-focus (DOF) is desirable to allow the entire corneal structure to be imaged. Such imaging is desirable in, for example, support of cornea transplant procedures. Likewise, imaging of the crystalline lens, REGION 2, benefits from high resolution imaging of the capsular structure. The capsular structure or bag (lens capsule) is the structure that holds the lens in a central position within the eye. The capsular structure generally includes an anterior and posterior capsule. A large DOF is generally required to visualize the entire lens at one time. By contrast, structures on the retina, REGION 3, lie in a constrained depth region, and tend to be very fine. Thus, retinal imaging typically requires very high resolution, but not necessarily a large DOF.

Although embodiments are discussed herein with example of a cornea, embodiments of the present inventive concept are not limited thereto. Systems, methods and compute program products discussed herein may be used with respect to any convex surface, for example, spherical, aspherical, cornea, contact lens, interocular lens and the like. Whatever the sample, embodiments of the present inventive concept may be used to determine the true APEX thereof.

Figure 2:
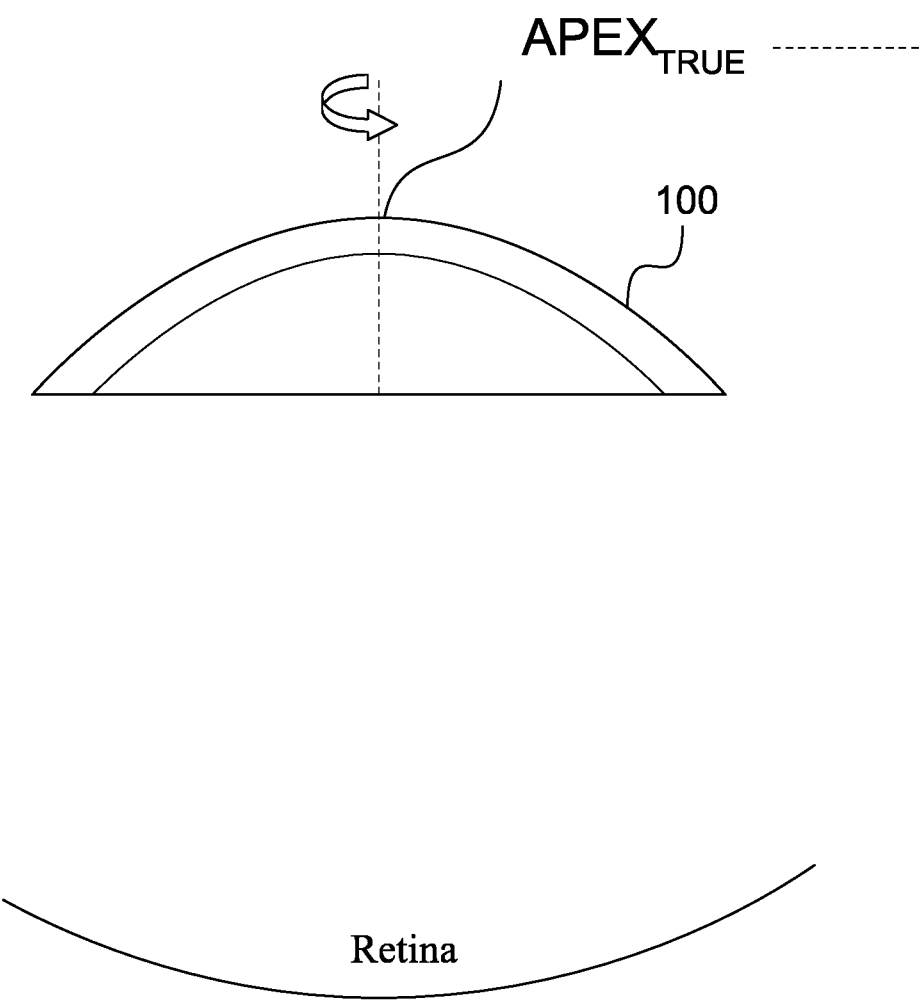
FIG. 2 is a diagram illustrating an ideal imaging scan around an actual APEX of a cornea.
Figure 3:
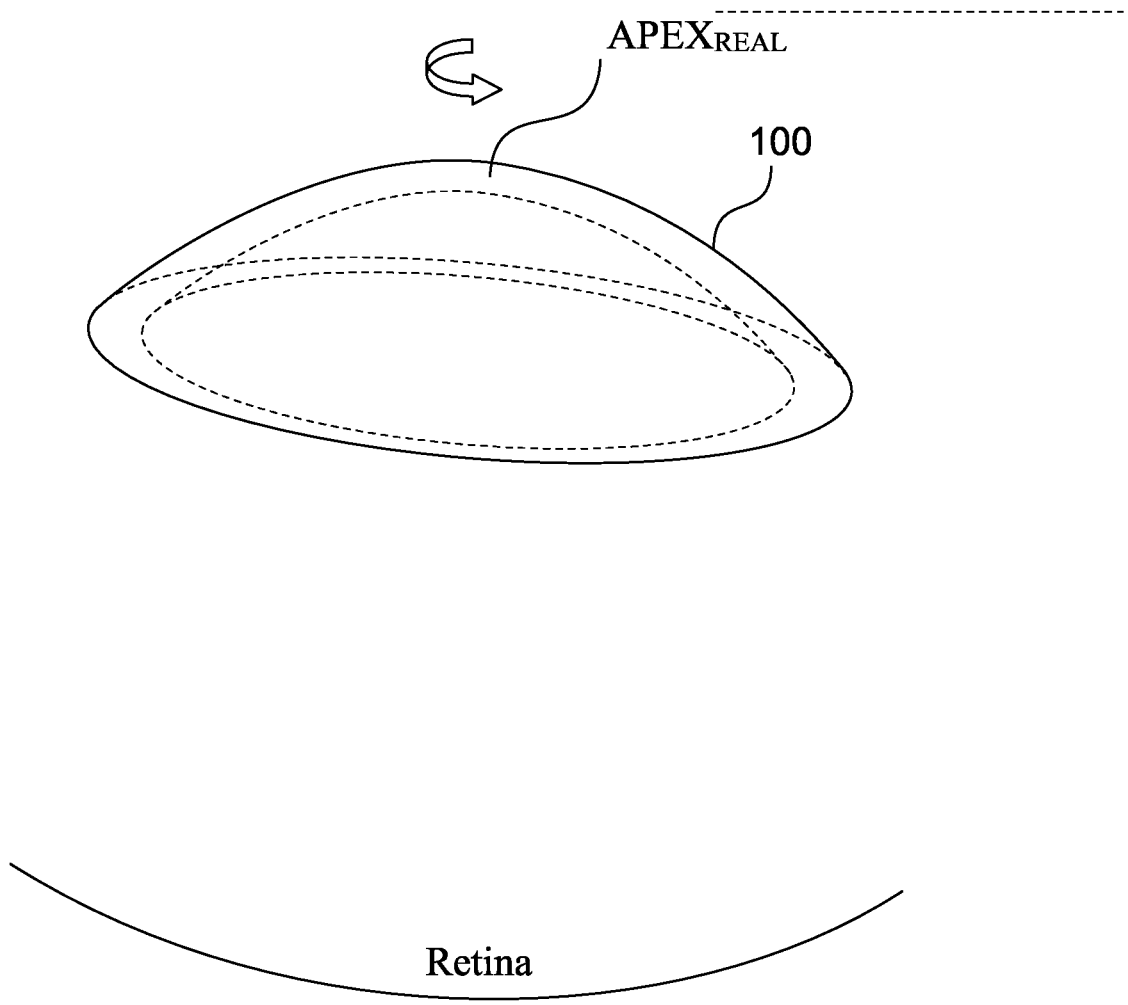
FIG. 3 is a diagram illustrating a non-ideal APEX during a rotational scan.

Referring now to FIG. 2, a diagram illustrating an "ideal" scanning of a cornea, as depicted in REGION 1 of FIG. 1, will be discussed. In particular, when the sample is a cornea 100 of an eye and it is scanned, ideally the scan rotation or origin will be centered at the $APEX_{TRUE}$ which is defined by the ANSI Z80.23 Standard as "[t]he location on the corneal surface, of a normal cornea, where the mean of the local principle curvatures is greatest." FIG. 2 illustrates the ideal position of the apex. However, as illustrated in FIG. 3, in reality when the cornea is scanned, the $APEX_{REAL}$ is not co-located with $APEX_{TRUE}$ due to misalignment or eye motion and, therefore, the APEX of the cornea is not at the center of each scan during image acquisition. For example, as discussed, just the pulsing of the blood through the eye may cause motion. The off-axis situation is illustrated in FIG. 3. A specular reflection artifact or "Perkinje reflection" may be present as a result of normal incidence of illumination from the OCT beam with respect to the curvature of the cornea. This reflection can be used to determine the optical axis of the OCT scanning beam, but in the case of off-axis imaging it may not take place at the $APEX_{TRUE}$ location of the cornea.

Figure 4:
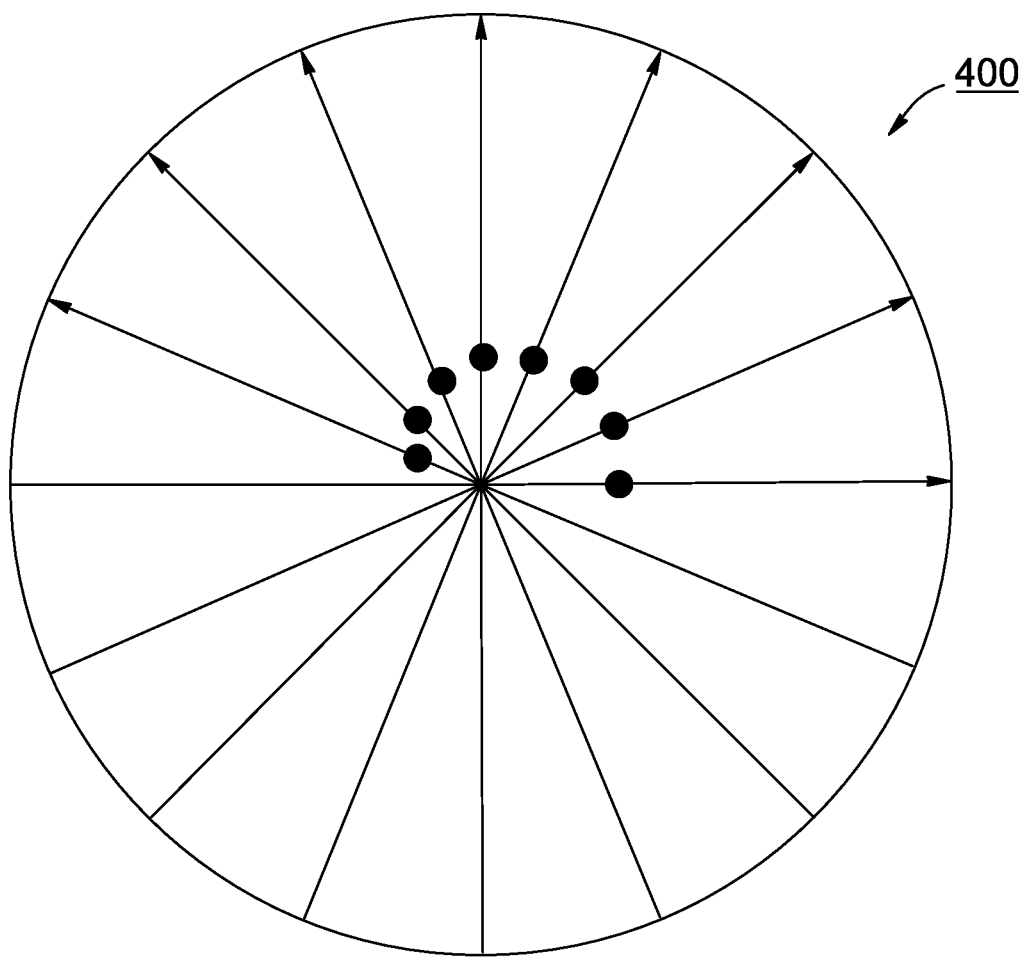
FIG. 4 is a diagram of an ellipse obtained from a scanned image.

When viewed from above (looking down on the image), all the APEX points may be plotted and the series of plotted points form an ellipse or partial ellipse 400 as illustrated in, for example, FIG. 4. It should be noted that only a partial ellipse is formed when imaging off-axis on a stationary sample. Conventionally, it was assumed that the center of the ellipse (C) was the actual $APEX_{TRUE}$ of the cornea. Then all the points in the ellipse would be registered to the center point C. However, this assumption was incorrect. In fact, it has been determined according to some embodiments of the present inventive concept discussed herein, that the $APEX_{TRUE}$ of the cornea (sample), i.e., the center is actually one of the points on the ellipse or partial ellipse 400. Accordingly, methods, systems and computer program products are provided herein to locate the actual center (the $APEX_{TRUE}$) and calculate an offset based on the actual center, not the center of the ellipse. Then, the remaining points on the ellipse can be mapped (registered) to the actual center. The scan parameters can then be adjusted accordingly so that scan center is on the $APEX_{TRUE}$ of the cornea and, if desired, a new scan can be taken with the $APEX_{TRUE}$ of the cornea at the center of rotation for the scan. If a new scan is not desired, the offset data can be used to adjust the angle of incidence value in the refractive calculation.

As will be discussed further below, some embodiments of the present inventive concept provide methods, systems and computer program products for identifying the APEX of the cornea, calculating the positional offset of each b-scan cornea APEX and remapping all APEX points to the true cornea Apex to reduce noise in the cornea thickness calculations.

Figure 5:
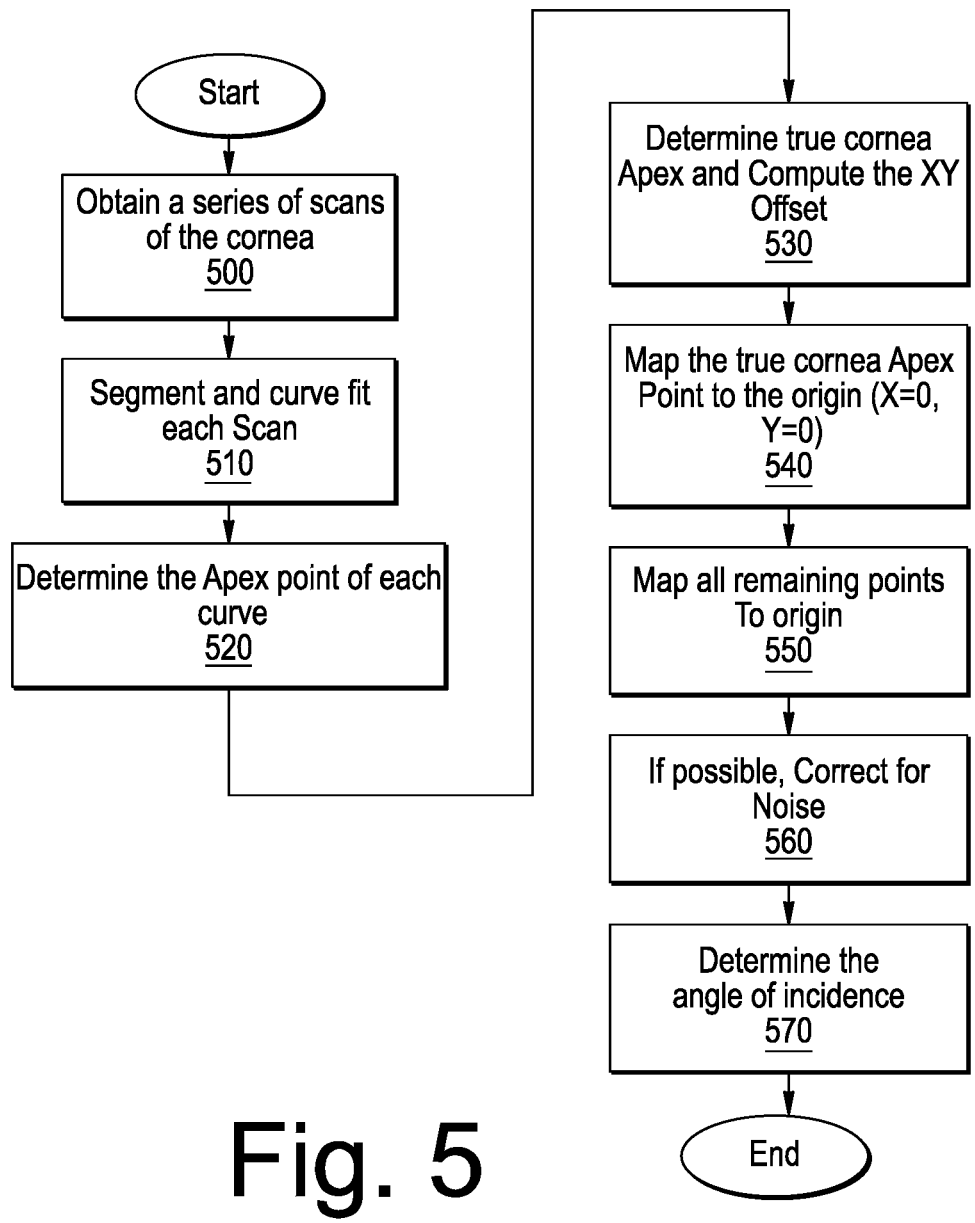
FIG. 5 is a flowchart illustrating operations in accordance with various embodiments of the present inventive concept.

Referring first to FIG. 5, operations for off-axis imaging will be discussed. As illustrated in FIG. 5, operations begin at (block 500) by obtaining a series of cornea scans. It will be understood that the image (a series of b-scans) is obtained by a radial scan with a rotation axis that is not necessarily around the actual APEX of the cornea. This aspect of the present inventive concept leads to correction of the off-axis APEX for each b-scan to the true center Apex of the cornea ($APEX_{TRUE}$). Once the scan is complete, the images are segmented, and curve fit to determine the cornea surface (block 510). The Apex for each curve is computed (block 520) and the $APEX_{TRUE}$ point is determined by the derivative of least value (block 530). As discussed above, the APEX points will form an ellipse or partial ellipse 400 if plotted and therefore the point which corresponds to the $APEX_{TRUE}$ point must be determined. In some embodiments, the $APEX_{TRE}$ of the cornea is determined using a mathematical equation.

In particular, consider the upper half of a standard ellipsoid in Cartesian coordinates:

$$z = c\sqrt{1 - \frac{x^2}{a^2} - \frac{y^2}{b^2}}, \quad \text{(Eq. 1)}$$

$a, b, c > 0$

With domain $\Omega=\{(x,y)\in \mathbb{R}^2 | x^2/a^2+y^2/b^2\leq 1\}$, the maximum z-value of this surface will occur at the origin. $\Omega$ defines the set of points (x,y) in real coordinate space of two dimensions that lie in the upper half of a standard ellipsoid and satisfy Eq. 1. Given a second point $(x_0,y_0)\in \Omega$, the locus of points satisfying (1) whose z-value ("height") is a maximum along any two-dimensional cross-section parallel to the z-axis and containing $(x_0,y_0)$ may be identified. Thus, it will be understood that the points in the ellipse come from calculating the value z using Eq. 1. This represents the highest elevation point in each B-scan image. Therefore, the z point for each B-scan creates the ellipse of points when viewed as a volume.

Figure 6:
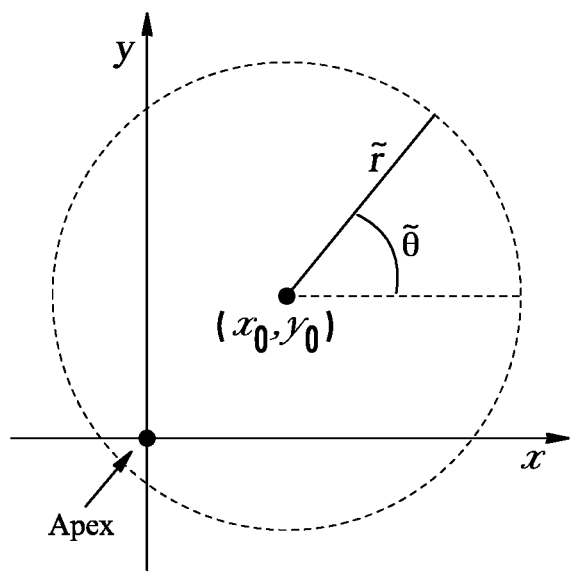
FIG. 6 is a diagram illustrating a local polar coordinate system not centered at the origin according to some embodiments of the present inventive concept.
Figure 7:
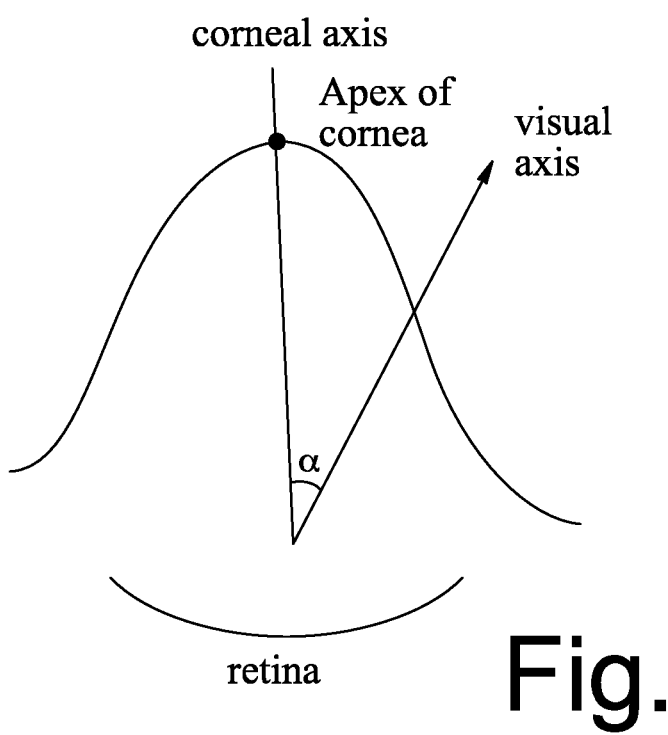
FIG. 7 is a diagram illustrating an angle between an APEX axis of the cornea and a visual axis in accordance with some embodiments of the present inventive concept.

To solve this problem, a local coordinate system is defined in polar coordinates as illustrated in FIG. 6, such that:

$$x - x_0 = \tilde{r} \cos \tilde{\theta}; \text{ and} \quad \text{(Eq. 2)}$$

$$y - y_0 = \tilde{r} \sin \tilde{\theta} \quad \text{(Eq. 3)}$$

where $(\tilde{r}, \tilde{\theta})$ is the polar coordinate where $\tilde{r}$ is the local radial coordinate and $\tilde{\theta}$ is an angle.

By applying the new coordinate system and fixing $\tilde{\theta}=\tilde{\theta}_k$, the height of a specific cross-section can be represented as a function of the local radial coordinate $\tilde{r}$:

$$F_{\tilde{\theta}_k}(\tilde{r}) = c\sqrt{1 - \frac{(x_0 + \tilde{r}\cos\tilde{\theta}_k)^2}{a^2} - \frac{(y_0 + \tilde{r}\sin\tilde{\theta}_k)^2}{b^2}}. \quad \text{(Eq. 4)}$$

where $F_{\tilde{\theta}_k}(\tilde{r})$ is the function in polar coordinate form that represents the height of a cross-section, which is equivalent to z in Cartesian coordinates in Eq. 1.

Represented more simply as follows:

$$F_{\tilde{\theta}_k}(\tilde{r}) = c\sqrt{\alpha - 2\tilde{r}\beta - \tilde{r}^2\gamma}, \quad \text{(Eq. 5)}$$

where:

$$\alpha \equiv 1 - \frac{x_0^2}{a^2} - \frac{y_0^2}{b^2},$$

$$\beta \equiv \frac{x_0\cos\tilde{\theta}_k}{a^2} + \frac{y_0\sin\tilde{\theta}_k}{b^2}, \quad \text{(Eqs. 6-8)}$$

$$\gamma \equiv \frac{\cos^2\tilde{\theta}_k}{a^2} + \frac{\sin^2\tilde{\theta}_k}{b^2}.$$

The maximum value of (5) occurs when:

$$F'_{\tilde{\theta}_k}(\tilde{r}) = \frac{-c(\beta + \gamma\tilde{r})}{\sqrt{\alpha - 2\tilde{r}\beta - \tilde{r}^2\gamma}} = 0; \quad \text{(Eq. 9)}$$

and $$F''_{\tilde{\theta}_k}(\tilde{r}) = \frac{-c(\beta^2 + \alpha\gamma)}{(\alpha - 2\tilde{r}\beta - \tilde{r}^2\gamma)^{3/2}} < 0, \quad \text{(Eq. 10)}$$

where $F_{\tilde{\theta}_k}'(\tilde{r})$ and $F_{\tilde{\theta}_k}''(\tilde{r})$ are the first and second derivatives of $F_{\tilde{\theta}_k}(\tilde{r})$, respectively.

To see that (Eq. 10) holds everywhere (Eq. 9) is defined (specifically, $\alpha-2\tilde{r}\beta-\tilde{r}^2\gamma>0$), it is noted that c>0. Thus, this problem is equivalent to showing that $\beta^2+\alpha\gamma>0$. Since $(x_0,y_0)$ is in the domain of the ellipsoid, it follows from (1) that $\alpha\geq 0$, with $\alpha=0$ occurring only when z=0—i.e., $F_{\tilde{\theta}_k}(\tilde{r})=0$ for a specific cross-section. But $F_{\tilde{\theta}_k}(\tilde{r})=0$ implies $\alpha-2\tilde{r}\beta-\tilde{r}^2\gamma=0$, which contradicts the assumption that the first derivative is defined. So $\alpha$ must be strictly positive. $\gamma$ is also strictly positive for $\tilde{\theta}_k\in \mathbb{R}$; hence $\beta^2+\alpha\gamma>0$ and (4) holds for all allowed values of $\tilde{r}$.

Therefore, the unique critical point:

$$\tilde{r}_k = -\beta/\gamma \quad \text{(Eq. 11)}$$

given by (9) represents the maximum height $z_k=F_{\tilde{\theta}_k}(\tilde{r}_k)$. Applying a change of coordinates back to the original Cartesian system illustrates that all set of all such points $(x_k,y_k,z_k)$ must satisfy the constraint:

$$1 = \frac{\left(x_k - \frac{1}{2}x_0\right)^2}{\left(\frac{b^2x_0^2 + a^2y_0^2}{4b^2}\right)} + \frac{\left(y_k - \frac{1}{2}y_0\right)^2}{\left(\frac{b^2x_0^2 + a^2y_0^2}{4a^2}\right)}, \quad \text{(Eq. 12)}$$

which is the formula for an ellipse centered halfway between the origin and $(x_0,y_0)$. The element $\tilde{r}_k$ is the local radial coordinate such that $F_{\tilde{\theta}_k}(\tilde{r}_k)$ is the maximum value of the function $F_{\tilde{\theta}_k}(\tilde{r})$. Similarly $z_k$ is the maximum value of Eq. 1 in Cartesian coordinates. $(x_k,y_k,z_k)$ is the Cartesian coordinate that satisfies all the constraints and results in the maximum height in the volume (collection of B-scans) or $APEX_{TRUE}$.

Thus, the equations set out above may allow the actual true APEX of the cornea to be located within the ellipse (block 530). An offset XY may be calculated (block 530) and this offset may be used to map $APEX_{TRUE}$ point to the origin (block 540). Further, all remaining calculated Apex points may be mapped to the $APEX_{TRUE}$ position as well (block 550).

Once the offsets are computed, an assessment of noise is made (block 560). Simply stated, if a degree of noise present is tolerable, the b-scan Apex point may be remapped to the $APEX_{TRUE}$ of the cornea using its respective offset. However, if the noise is not tolerable, i.e. the calculated b-scan Apex point does not fall along the ellipse criteria then the scan is discarded from the data set to calculate the cornea thickness. Alternatively, the imaging system may be configured to auto shift the scan origin to the $APEX_{TRUE}$ position and reimage.

There are at least two types of noise, random noise and non-random noise which can impact the curve fitting algorithm and thus the calculated Apex points. Random noise stems from bulk motion such as eye movement, pulsations of the eye or saccade. Non-random noise typically comes from fit errors and results in an Apex point not being located on the ellipse of Apex points. If there is too much random noise in an image, the subject many be reimaged to obtain an image with less random noise. Non-random noise can be removed using extrapolation from neighboring b-scans.

In some embodiments, once the offset has been determined, the angle of incidence can be calculated and applied to the refractive calculation and thickness measurement for improved accuracy (block 570). As used herein, the "angle of incidence" is the arctangent of the slope of the curve at the location of the scanning beam. Once one of the points on the ellipse has been identified as $APEX_{TRUE}$, $(x_{TRUE}, y_{TRUE})$, then the angle of incidence can be calculated as:

$$\theta_i = \arctan(y_{TRUE}/x_{TRUE}). \quad \text{(Eq.13)}$$

It will be understood that although examples are discussed herein using the cornea and an OCT imaging system, embodiments of the present inventive concept are not limited to this configuration. Any subject and/or imaging system using a radial pattern may benefit from the inventive concept without departing from the scope of the inventive concept. For example, this technique can be applied to locating the optical axis of an interocular lens in situ to aid in interocular lens (IOL) placement.

In particular, embodiments of the present inventive concept may be used in Optical Coherence Tomography (OCT) imaging systems. These systems may be included in ophthalmic surgical microscopes as discussed, for example, in U.S. Pat. No. 8,777,412, the contents of which are hereby incorporated herein by reference as if set forth in its entirety. These imaging systems may be used in various types of surgeries including cataract surgery. They also may be used to image a contact lens as discussed in, for example, U.S. Patent Application No. 2015/0168250, the contents of which are incorporated herein by reference as if set forth in its entirety.

Figure 8A:
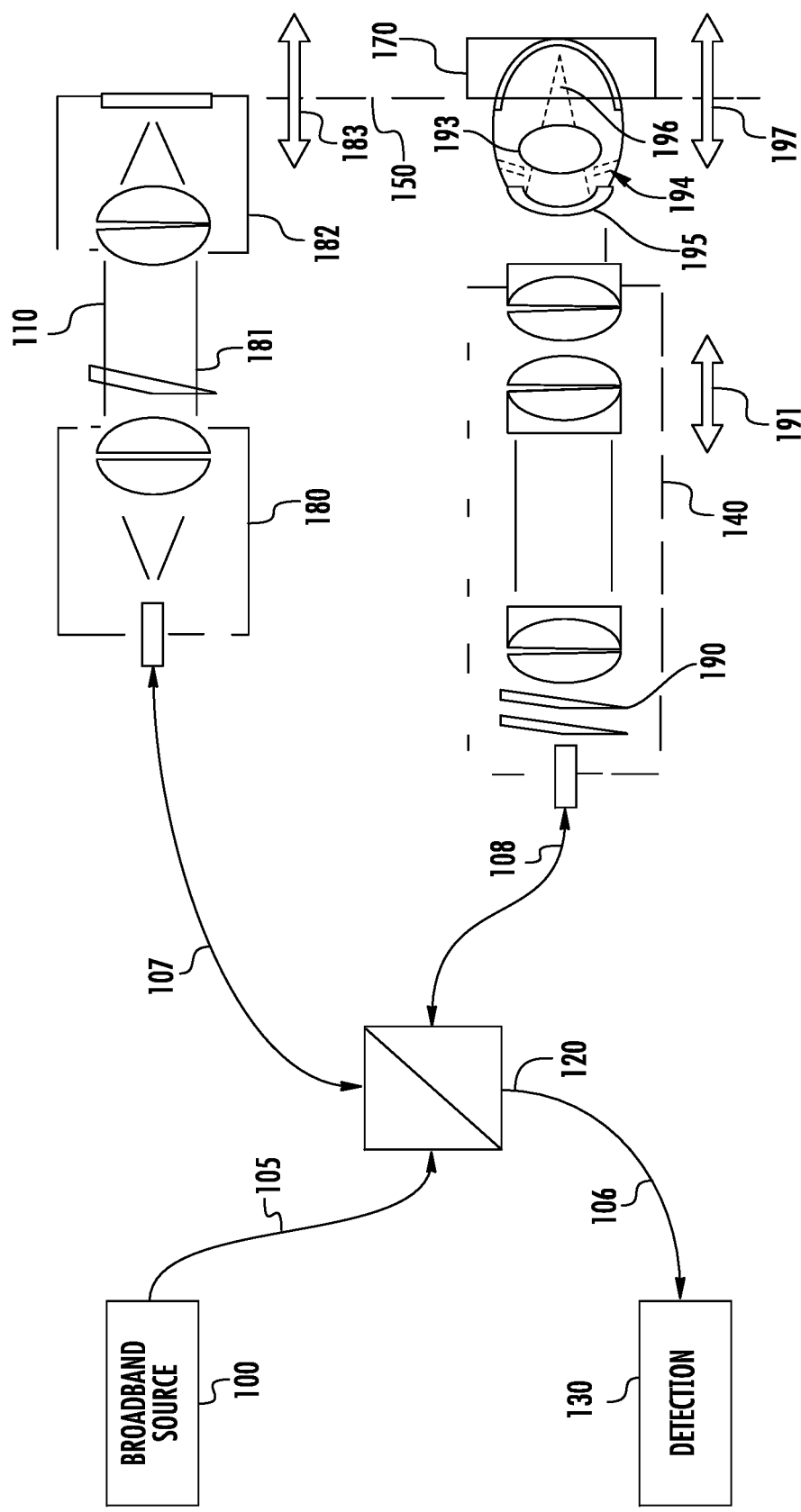
FIG. 8A is a block diagram illustrating an example OCT retinal (posterior) imaging system.

Example imaging systems for use in accordance with some embodiments of the present inventive concept will now be discussed with respect to FIGS. 8A and 8B. It will be understood that these systems are provided for example purposes only and, thus, embodiments of the present inventive concept should not be limited thereto. Conventional Fourier domain OCT (FDOCT) systems will now be discussed to provide some background related to these systems. Referring first to FIG. 8A, a block diagram of an FDOCT retinal imaging system will be discussed. As illustrated in FIG. 8A, the system includes a broadband source 100, a reference arm 110 and a sample arm 140 coupled to each other by a beamsplitter 120. The beamsplitter 120 may be, for example, a fiber optic coupler or a bulk or micro-optic coupler. The beamsplitter 120 may provide from about a 50/50 to about a 90/10 split ratio. As further illustrated in FIG. 8A, the beamsplitter 120 is also coupled to a wavelength or frequency sampled detection module 130 over a detection path 106 that may be provided by an optical fiber.

As further illustrated in FIG. 8A, the source 100 is coupled to the beamsplitter 120 by a source path 105. The source 100 may be, for example, a continuous wave broadband superluminescent diode, a pulsed broadband source, or tunable source. The reference arm 110 is coupled to the beamsplitter 120 over a reference arm path 107. Similarly, the sample arm 140 is coupled to the beamsplitter 120 over the sample arm path 108. The source path 105, the reference arm path 107 and the sample arm path 108 may all be provided by optical fiber or a combination of optical fiber, free-space, and bulk- or micro-optical elements.

As illustrated in FIG. 8A, the reference arm of the FDOCT retinal imaging system may include a collimator assembly 180, a variable attenuator 181 that may include a neutral density filter or a variable aperture, a mirror assembly 182, a reference arm variable path length adjustment 183 and a path length matching position 150, i.e. optical path length matching between the reference arm path length and the sample arm path length to the subject region of interest. As further illustrated, the sample arm 140 may include a dual-axis scanner assembly 190 and an objective lens with variable focus 191.

The sample illustrated in FIG. 8A is an eye including a cornea 195, iris/pupil 194, ocular lens 193 and retina 196. A representation of an FDOCT imaging window 170 is illustrated near the retina 196. The retinal imaging system relies on the objective lens plus the optics of the subject eye, notably cornea 195 and ocular lens 193, to image the posterior structures of the eye. As further illustrated the region of interest 170 within the subject is selected through coordination of the focal position 196 and reference arm path length adjustment 183, such that the path length matching position 197 within the subject is at the desired location.

Figure 8B:
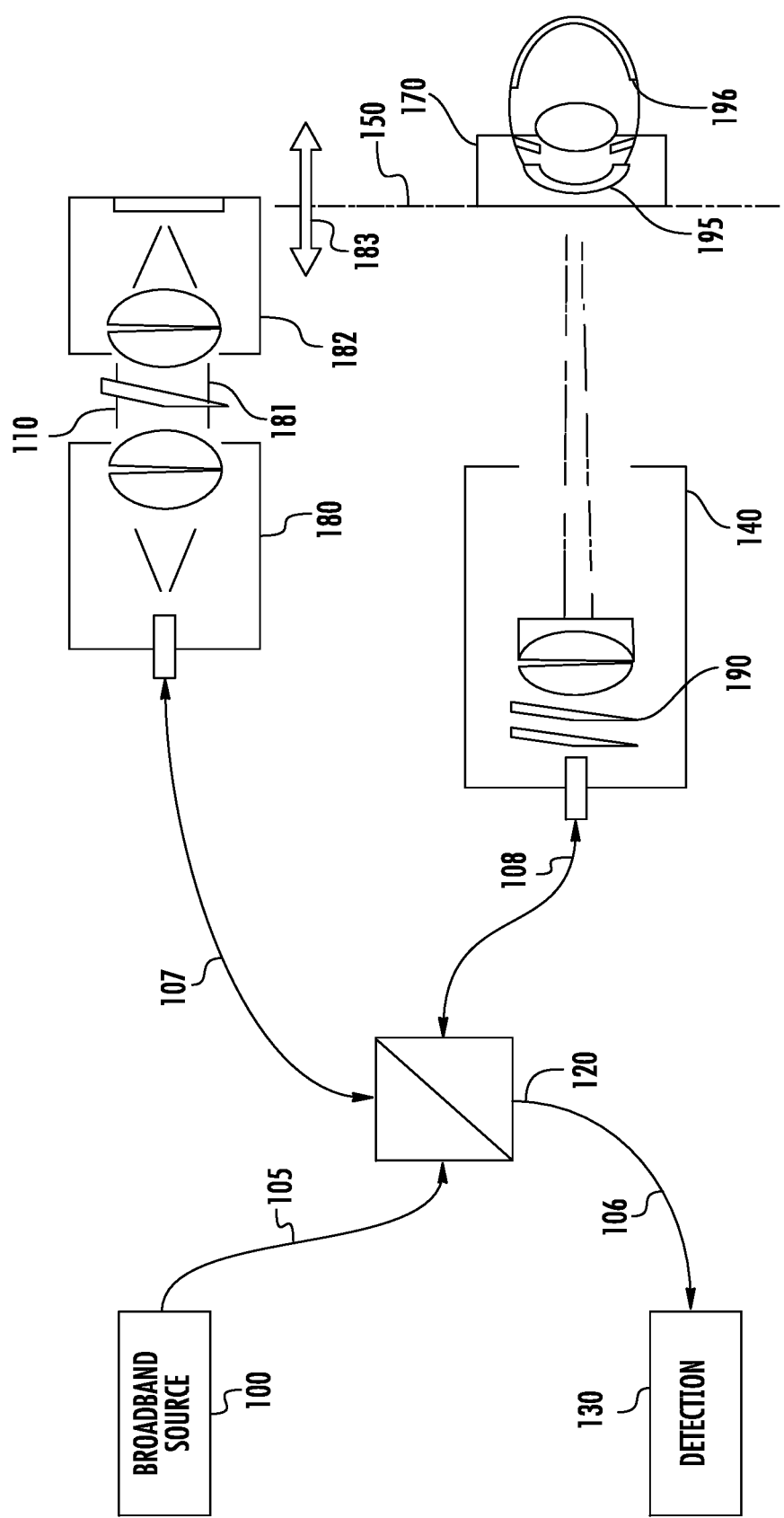
FIG. 8B is a block diagram illustrating an example Optical Coherence Tomography (OCT) cornea (anterior) imaging system.

Referring now to FIG. 8B, a block diagram illustrating a FDOCT corneal (anterior) imaging system will be discussed. As illustrated therein, the system of FIG. 8B is very similar to the system of FIG. 8A. However, the objective lens variable focus need not be included, and is not included in FIG. 8B. The anterior imaging system of FIG. 8B images the anterior structures directly, without reliance on the optics of the subject to focus on the anterior structures.

Some embodiments of the present inventive concept may be used to align an OCT scan to the center of the relay lens in retinal viewing lens systems. Given the high degree of variability in alignment of third-party retinal viewing lens systems used in conjunction with ophthalmic surgical microscopes, the absolute location of the optical axis of the lens system is unknown. In addition, the disinfection process used to clean the devices can result in slightly bent or deformed components rendering the original lens location relative to the optical axis of the surgical microscope obsolete. Therefore, the origin of the OCT scan is generally re-centered relative to the center of the retina viewing lens system before surgery.

In further embodiments of the inventive concept, the location of the center of the retinal viewing optics may be used to offset the OCT scan beam to a location coincident with the surgical microscope ocular camera view.

Figure 9:
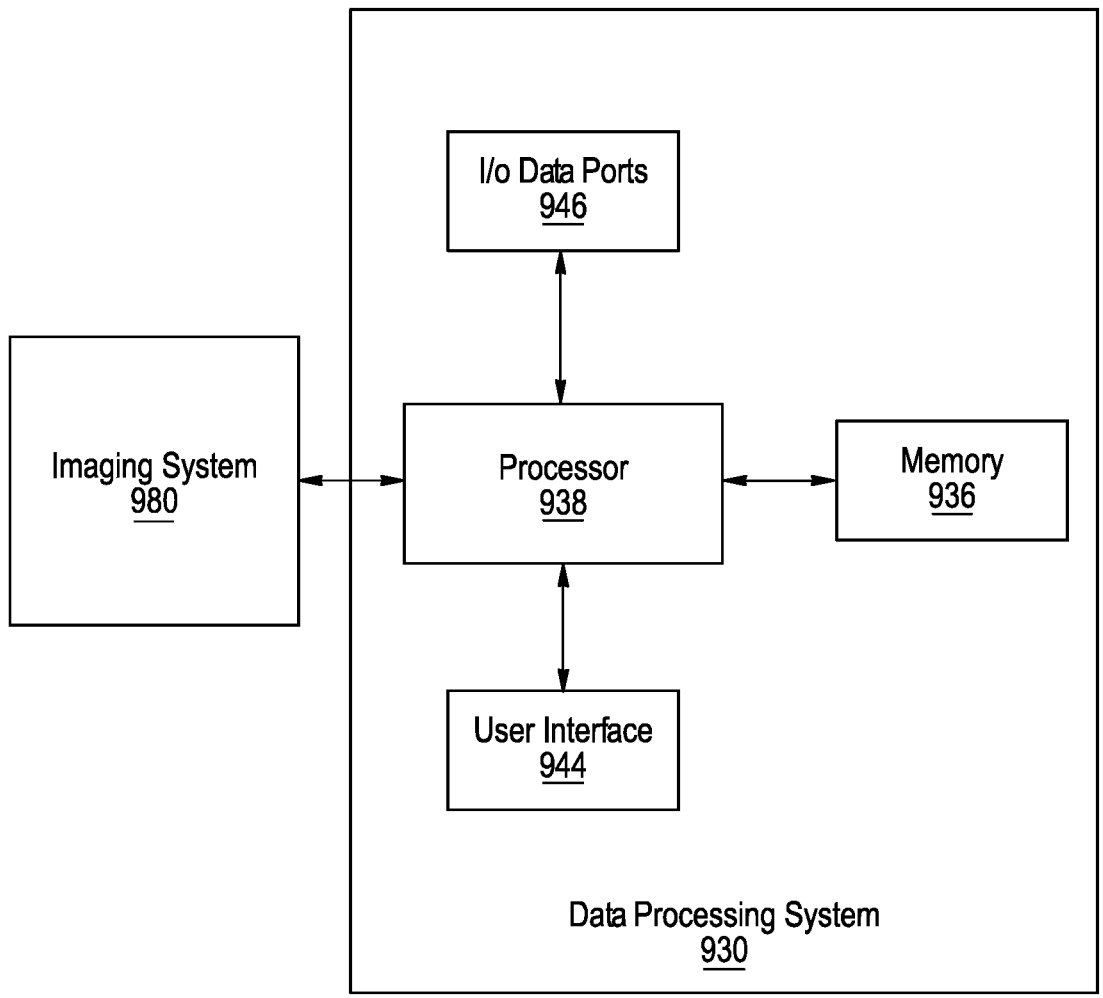
FIG. 9 is a block diagram of a system including an imaging system and data processing system in accordance with various embodiments of the present inventive concept.

As is clear from the discussion of embodiments of the present inventive concept above, many of the methods discussed herein require processing provided by a computing device. Referring now to FIG. 9, example embodiments of a data processing system 930 configured in accordance with embodiments of the present inventive concept will be discussed with respect to FIG. 9. As will be understood, the data processing system 930 may be included in the system of, for example, FIGS. 8A through 8B, or may be a separate device that communications with the system in FIGS. 8A and 8B without departing from the scope of the present inventive concept. The data processing system 930 may include a user interface 944, including, for example, input device(s) such as a keyboard or keypad, a display, a speaker and/or microphone, and a memory 936 that communicate with a processor 938. The data processing system 930 may further include I/O data port(s) 946 that also communicates with the processor 938. The I/O data ports 946 can be used to transfer information between the data processing system 930 and another computer system or a network using, for example, an Internet Protocol (IP) connection. These components may be conventional components such as those used in many conventional data processing systems, which may be configured to operate as described herein.

As further illustrated in FIG. 9, as discussed above, the data processing system 930 may be in communication with an imaging system 980. The imaging system 980 may be separate from or part of the data processing system 930 without departing from the scope of the present inventive concept. As discussed above, the imaging system 980 may be an OCT imaging system, for example, the systems illustrated in FIGS. 8A and 8B, or another type of imaging system without departing from the scope of the present inventive concept.

The flowchart and block diagrams in the Figures illustrate the architecture, functionality, and operation of possible implementations of systems, methods and computer program products according to various aspects of the present disclosure. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The description of the present disclosure has been presented for purposes of illustration and description but is not intended to be exhaustive or limited to the disclosure in the form disclosed. Many modifications and variations will be apparent to those of ordinary skill in the art without departing from the scope and spirit of the disclosure. The aspects of the disclosure herein were chosen and described in order to best explain the principles of the disclosure and the practical application, and to enable others of ordinary skill in the art to understand the disclosure with various modifications as are suited to the particular use contemplated.

That which is claimed is:

1. A system for determining an apex of curvature in an image obtained from a sample, the system comprising:
   an imaging system configured to obtain a plurality of scans of a sample; and
   a processor associated with the imaging system, the processor configured to:
      segment and curve fit each respective scan of the plurality of scans to a surface of the sample to determine a respective apex, wherein each respective scan is along a respective radial line at a respective angle in a polar coordinate system, an origin of the polar coordinate system being off of a corneal axis;
      determine a true apex among the determined apexes using a derivative of least value;
      calculate an XY offset based on the determined true apex;
      map the true apex to an origin where X and Y are equal to zero; and
      adjust the coordinates associated with remaining apexes not-determined to be not the true apex based on the calculated offset.

2. The system of claim 1, wherein after calculating the offset, the processor is further configured to:
   assess a degree of random noise present in the plurality of scans; and
   if the random noise present is determined to be not tolerable, the imaging system is configured to auto-shift a scan origin based on the calculated offset and rescan the sample, or discard the plurality of scans and rescan the sample.

3. The system of claim 1, wherein the processor is further configured to:
   calculate an arctangent of a slope of a curve of a scanning beam of the imaging system to provide an angle of incidence; and
   apply the angle of incidence to a refractive calculation and thickness measurement.

4. The system of claim 1, wherein the imaging system is configured to obtain the plurality of scans using a radial scan with a rotation axis.

5. The system of claim 1, wherein the processor is further configured to plot each of the determined apexes for each curve associated with each of the plurality of scans to create an ellipse when plotted on an XY coordinate plane and wherein one of plotted apexes comprises the true apex.

6. The system of claim 1, wherein the sample is a cornea of an eye of a subject.

7. The system of claim 1, wherein the imaging system comprises an optical coherence tomography imaging system.

8. A method for determining an apex of curvature in an image obtained from a sample, the method comprising:
   obtaining a plurality of scans of a sample;
   segmenting and curve fit each respective scan of the plurality of scans to a surface of the sample to determine a respective apex, wherein each respective scan is along a respective radial line at a respective angle in a polar coordinate system, an origin of the polar coordinate system being off of a corneal axis;
   determining a true apex among the determined apexes using a derivative of least value;
   calculating an XY offset based on the determined true apex;
   mapping the true apex to an origin where X and Y are equal to zero; and
   adjusting the coordinates associated with remaining apexes determined to be not the true apex based on the calculated offset,
   wherein at least one of the obtaining, segmenting, determining a true apex, calculating, mapping and adjusting are performed by at least one processor.

9. The method of claim 8, further comprising, following the calculating the offsets:
   assessing a degree of random noise present the plurality of scans; and
   if the random noise present is determined to be not tolerable, auto-shifting a scan origin based on the calculated offset and rescanning the sample or discarding the plurality of scans and rescanning the sample.

10. The method of claim 8, further comprising:
   calculating an arctangent of a slope of a curve of a scanning beam of the imaging system to provide an angle of incidence; and
   applying the angle of incidence to a refractive calculation and thickness measurement.

11. The method of claim 8, wherein the plurality of scans are obtained using a radial scan with a rotation axis.

12. The method of claim 8, further comprising plotting each of the determined apexes for each curve associated with each of the plurality of scans to create an ellipse when plotted on an XY coordinate plane and wherein one of plotted apexes comprises the true apex.

13. The method of claim 8, wherein the sample is a cornea of an eye of a subject.

14. The method of claim 8, wherein obtaining the plurality of scans comprises obtaining the plurality of scans using an optical coherence tomography imaging system.

15. A computer program product for determining an apex of curvature in an image obtained from a sample, the computer program product comprising:
   a non-transitory computer-readable storage medium having computer-readable program code embodied: in the medium, the computer-readable program code comprising:
   computer readable program code to obtain a plurality of scans of a sample;

computer readable program code to segment and curve fit each respective scan of the plurality of scans to a surface of the sample to determine a respective apex, wherein each respective scan is along a respective radial line at a respective angle in a polar coordinate system, an origin of the polar coordinate system being off of a corneal axis;

computer readable program code to determine a true apex among the determined apexes using a derivative of least value;

computer readable program code to calculate an XY offset based on the determined true apex;

computer readable program code to map the true apex to an origin where X and Y are equal to zero; and computer readable program code to adjust the coordinates associated with remaining apexes determined to be not the true apex based on the calculated offset, wherein at least one of the obtaining, segmenting, determining a true apex, calculating, mapping and adjusting are performed by at least one processor.

16. The computer program product of claim 15, further comprising:

computer readable program code to assess a degree of random noise present in the plurality of scans; and computer readable program code to auto-shift a scan origin based on the calculated offset and rescan the sample or computer readable program code to discard the plurality of scans and rescan the sample if the random noise present is determined to be not tolerable.

17. The computer program product of claim 15, further comprising:

computer readable program code to calculate an arctangent of a slope of a curve of a scanning beam of the imaging system to provide an angle of incidence; and computer readable program code to apply the angle of incidence to a refractive calculation and thickness measurement.

18. The computer program product of claim 15, wherein the plurality of scans are obtained using a radial scan with a rotation axis.

19. The computer program product of claim 15, further comprising computer readable program code to plot each of the determined apexes for each curve associated with each of the plurality of scans to create an ellipse, when plotted on an XY coordinate plane and wherein one of plotted apexes comprises the true apex.

20. The computer readable program code of claim 15, wherein the sample is a cornea of an eye of a subject and wherein the computer readable program code to obtain the plurality of scans comprises computer readable program code to obtain the plurality of scans using an optical coherence tomography imaging system.

* * * * *